United States Patent [19]

Turner

[11] Patent Number: 5,601,534
[45] Date of Patent: Feb. 11, 1997

[54] DISPOSABLE HYPODERMIC SYRINGE AND NEEDLE COMBINATION

[75] Inventor: Raymond A. Turner, Memphis, Tenn.

[73] Assignee: The University of Memphis, Memphis, Tenn.

[21] Appl. No.: 486,191

[22] Filed: Jun. 7, 1995

[51] Int. Cl.⁶ ..................................................... A61M 5/32
[52] U.S. Cl. .......................................... 604/195; 604/110
[58] Field of Search .................................... 604/110, 195, 604/187, 192, 198, 263

[56] References Cited

U.S. PATENT DOCUMENTS

| 4,770,655 | 9/1988 | Haber et al. . | |
|---|---|---|---|
| 4,850,968 | 7/1989 | Ramono . | |
| 4,880,410 | 11/1989 | Rossmark . | |
| 4,921,486 | 5/1990 | DeChellis et al. . | |
| 4,931,040 | 6/1990 | Haber et al. . | |
| 4,947,863 | 8/1990 | Haber et al. . | |
| 4,986,813 | 1/1991 | Blake, III et al. . | |
| 5,007,903 | 4/1991 | Ellard . | |
| 5,019,044 | 5/1991 | Tsao . | |
| 5,026,354 | 6/1991 | Kocses . | |
| 5,053,010 | 10/1991 | McGary et al. . | |
| 5,064,419 | 11/1991 | Gaarde . | |
| 5,125,898 | 6/1992 | Kaufhold, Jr. et al. . | |
| 5,232,458 | 8/1993 | Chen .......................................... | 604/195 |
| 5,273,539 | 12/1993 | Chen .......................................... | 604/110 |
| 5,507,117 | 3/1985 | Vining et al. . | |

Primary Examiner—John D. Yasko
Attorney, Agent, or Firm—Needle & Rosenberg, P.C.

[57] ABSTRACT

The present invention provides a disposable hypodermic syringe which has an elongate, rigid, hollow chamber with a longitudinal axis, a posterior opening and an anterior opening smaller than the posterior opening. The syringe also has a hollow needle axially disposed within the anterior opening. The first end of the needle is outside the chamber in fluid communication with an opposed second end. The second end of the needle is disposed within the chamber and in fluid communication therewith. The syringe also includes an axially slidable plunger in a fluid-tight seal within the chamber for drawing a fluid into the chamber through the first end of the needle and for expelling the fluid from the chamber through the second end of the needle. The plunger has a anterior end and a posterior end and comprises a grip for the user which extends out of the posterior opening of the chamber and a sloped surface for deflecting the second end of the needle during operation of the syringe. The plunger also includes a nipple for retracting the needle. Complementary to the plunger, the second end of the needle includes a surface for means for engaging the sloped surface on the plunger and a barb for engaging the nipple.

Methods of using the above disposable hypodermic syringe.

8 Claims, 5 Drawing Sheets

DISPOSABLE HYPODERMIC SYRINGE AND NEEDLE COMBINATION

BACKGROUND OF THE INVENTION

1. Field of the Invention

The invention relates to a disposable hypodermic syringe and needle combination designed to eliminate the hazard of accidental needle sticks. In particular, the invention relates to an apparatus for and method of retracting a needle into a syringe after injection so that the needle cannot be forced back out of the syringe.

2. Background Art

The disposal of contaminated hypodermic syringe needles has been and continues to be a major health concern. The Medical Waste Tracking Act of 1988 disclosed that injuries caused by discarded hypodermic needles are the cause of new human immunodeficiency virus (HIV) and hepatitis virus transmittals each year. Those at greatest risk are nurses, emergency medical personnel, medical waste handlers, dental assistants, physicians and dentists. An estimated 25,000 medical waste injuries are predicted annually, resulting in several deaths.

Disposable hypodermic syringes presently in use are distributed in two forms. One form of disposable hypodermic syringe has the hypodermic needle attached to the syringe and the other form requires that the needle be attached to the syringe just before use. In the operation of a conventional disposable hypodermic syringe, the procedure for preparing the syringe/needle assembly for injection is as follows: 1) the plunger is fully depressed into the syringe; 2) the needle is inserted into a vial containing the injectable material; 3) the plunger is withdrawn to a point indicating the prescribed volume of injectable material; 4) the syringe is positioned to place the needle in an upright position; 5) the plunger is depressed to the point where a drop of the injectable material emerges from the lumen of the needle in order to force trapped air out of the syringe; 6) the needle is inserted into the subject; and 7) the plunger is fully depressed, forcing the injectable material through the needle and into the subject.

After the hypodermic needle pierces the skin and is withdrawn, the needle requires disposal. Various inventions have attempted to address this problem including 1) procedures for the disposal of hypodermic needles; 2) designs for incorporation of a sheath that covers the needle abler the needle is used; and 3) designs for retracting the needle into the syringe after use. However, these procedures must be carried out properly and consistently by all persons involved in the disposal of hypodermic needles and are not foolproof. Although syringes with sheaths are presently being used, these types of syringes are more expensive due to unnecessary complexity, greater production costs and greater material requirements.

In addition to greater production costs and material requirements, an even more serious and potentially fatal problem exists in the design of most disposable syringes with retractable needles, which is the possibility of injecting air into a subject.

In previous designs for syringes with retractable needles, the needle is partially fixed inside the syringe to a depth sufficient for the needle to be captured by the plunger and subsequently withdrawn. This means that when the syringe is filled, the plunger cannot be fully depressed, to avoid premature capture of the needle. Consequently, there is always a space filled with air inside the syringe. Dispelling the air within the syringe is problematic. Because the needle is partially fixed inside the syringe, the air bubble cannot be fully driven out. The air bubble floats to the highest point in the syringe, precluding the possibility of positioning the air bubble at the inner opening of the needle, from where it can be expelled. However, in the course of injecting the material within the syringe into the subject, the plunger is fully depressed, expelling the trapped air bubble into the subject, with potentially fatal consequences.

Therefore, there exists a need for a disposable hypodermic syringe with a retractable needle, designed such that any air bubble in the syringe can be fully expelled prior to injection.

SUMMARY OF THE INVENTION

The present invention meets this need and provides substantial improvements. The present invention provides a disposable hypodermic syringe. The syringe has an elongate, rigid, hollow chamber with a longitudinal axis. The chamber has both a posterior opening and an anterior opening smaller than the posterior opening. The syringe further includes a hollow needle axially disposed within the anterior opening of the chamber. The needle has a first end outside the chamber in fluid communication with an opposed second end. The second end of the needle is disposed within the chamber and in fluid communication with the chamber. The syringe also includes axially slidable means sealingly engaged within the chamber for drawing a fluid into the chamber through the first end of the needle and for expelling the fluid from the chamber through the second end of the needle. This slidable means has a anterior end and a posterior end and also comprises a means for manually gripping extending out of the posterior opening of the chamber. Furthermore, the syringe includes a means for deflecting the second end of the needle during operation of the syringe and a means for retracting the needle. Also, the second end of the needle includes means for engaging a deflecting means and means for engaging a retracting means.

The present invention also provides a disposable hypodermic syringe as above described, where the means for drawing a fluid into and expelling it from the chamber comprises an elongate, axial rod disposed within the chamber and a piercable piston for forming a slidable seal within the chamber. In this embodiment, the piston is disposed within the chamber and between the anterior opening and an end of the elongate, axial rod and is operatively coupled to the elongate axial rod so that axial movement of the rod results in axial movement of the piston.

The present invention further provides a disposable hypodermic syringe as described, wherein the means for deflecting the second end of the needle comprises a nipple on the end of the rod disposed within the chamber. In this embodiment, the means for retracting the needle comprises a surface of the nipple facing the posterior opening of the hollow chamber and the means for engaging a deflecting means comprises a sloping cut in the second end of the needle disposed within the chamber. Also in this embodiment, the means for engaging a retracting means comprises a barb in a portion of the second end of the needle disposed within the chamber. The rod is operable to cause the piston to be pierced by the second end of the needle disposed within the chamber to bring the nipple into contact with the sloping cut, thereby radially biasing the second end of the needle disposed within the chamber.

The present invention also provides a method for retracting a needle into an elongate syringe after an injection so that the needle cannot be forced back out of the syringe. This method comprises the steps of piercing a flexible piston at an end of a plunger inside the syringe with an end of the needle inside the syringe. Then the user applies a radial bias to the end of the needle inside the syringe. This action engages a barb near the end of the needle inside the syringe with a nipple on the plunger. The user then retracts the needle through an opening in the syringe by retracting the plunger after the nipple is engaged with the barb so that the bias is relieved. Relief of this bias causes the needle to become misaligned with the opening in the syringe.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed. The accompanying drawings, which are incorporated in and constitute a part of this specification, illustrate several embodiments of the invention and together with the description, serve to explain the principles of the invention.

BRIEF DESCRIPTION OF THE DRAWINGS

FIG. 1D shows a side plan view of the syringe of the present invention where the needle is almost completely within the chamber but its axis is still parallel to that of the chamber.

FIG. 1E shows a side plan view of the syringe of the present invention where the needle is biased within the chamber and cannot be forced through the opening.

DETAILED DESCRIPTION OF THE PREFERRED EMBODIMENTS

The present invention may be understood more readily by reference to the following detailed description of preferred embodiments of the invention and to the Figures and their previous and following description.

Before the present devices and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

Throughout this application, various publications are referenced. The disclosures of these publications in their entireties are hereby incorporated by reference into this application in order to more fully describe the state of the art to which this invention pertains.

Figure 1A:
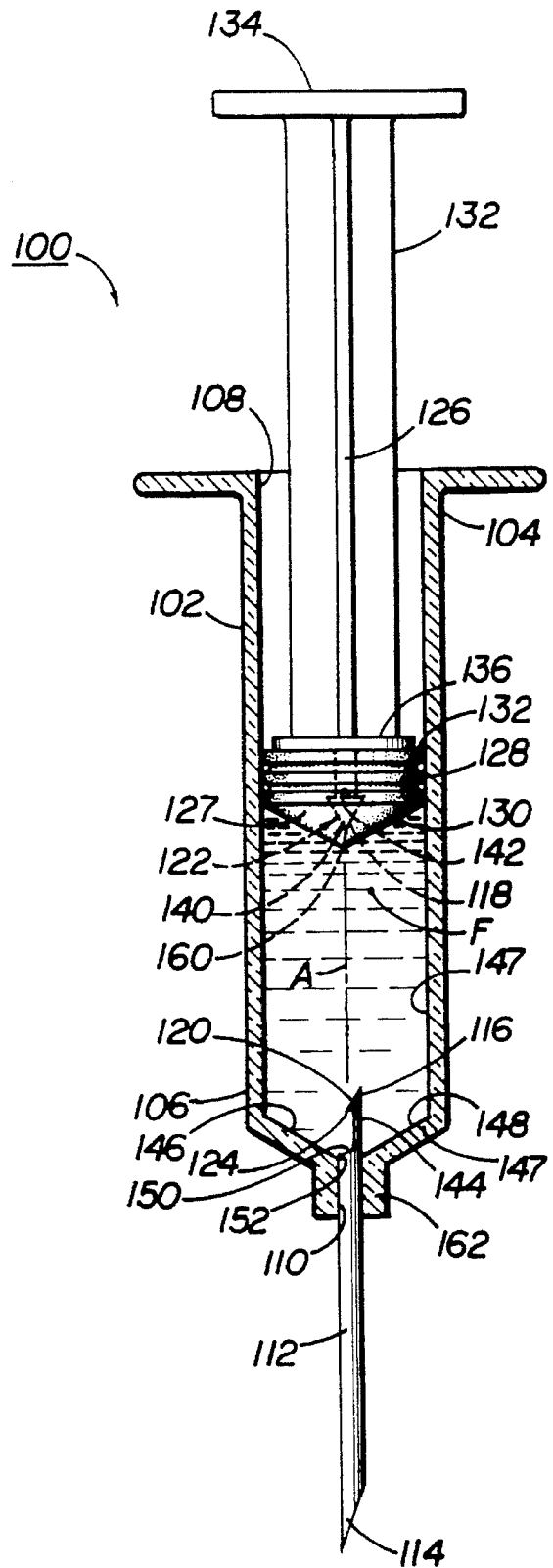
FIG. 1A shows a side plan view of the syringe of the present invention.

Referring now to FIGS. 1A through 1E and FIG. 2, especially FIG. 1A, in a preferable embodiment, the present invention provides a disposable hypodermic syringe 100. The syringe 100 has an elongate, rigid, hollow chamber 102 having a longitudinal axis A. The chamber 102 has a posterior opening 108 at a proximal end 104 and an anterior opening 110 at a distal end 106, the anterior opening 110 being smaller than the posterior opening 108, The syringe 100 also has a hollow needle 112 axially disposed within the anterior opening 110. The size of the needle 112 is not critical and will vary depending upon the application. The needle has a first end 114 outside the chamber 102 in fluid communication with an opposed second end 116. The second end 116 of the needle 112 is disposed within the chamber 102 and in fluid communication therewith. Thus, the first end 114 is the end which would pierce a patient's skin (not shown).

The second end 116 of the needle 112 includes means for engaging 120 a deflecting means 118 and means for engaging 124 a retracting means 122. These means are discussed more fully below.

The syringe 100 further includes an axially slidable means 128 sealingly engaged within the chamber 102 for drawing a fluid F into the chamber 102 through the first end 114 of the needle 112 and for expelling the fluid F from the chamber 102 through the second end 116 of the needle 112, the means for drawing and expelling 128 having a anterior end 130 and a posterior end 132. The seal prevents leakage of fluid F out of the chamber 102. The seal, upon operation, can create a partial vacuum through the needle 112 thereby drawing fluid F into the chamber 102 and also can create a positive pressure, thereby forcing the fluid F back out of the needle 112 and into the patient (not shown) or other destination (not shown).

The means for drawing and expelling 128 is made up of a means for manually gripping 134 extending out of the posterior opening 108 of the chamber 102. In a preferred embodiment, the means for gripping 134 comprises a thumb flange. The means for drawing and expelling 128 also includes a means for deflecting the second end 118 of the needle 112 during operation of the syringe 100. The means for deflecting the second end 118 of the needle 112 is located at the anterior end 130 of the means for drawing and expelling 128. The means for drawing and expelling 128 further includes a means for retracting 122 the needle 112. The means for deflecting the second end 118 of the needle 112 should be comprised of a rigid material.

In a preferred embodiment, the slidable means 128 of the disposable syringe 100 comprises an elongate, axial rod 126 disposed within the chamber 102 and a piercable piston 127 for forming a slidable seal within the chamber 102. The piston 127 may be comprised of rubber or silicone or any other suitable material generally known to those skilled in the art. The material should be selected so that the second end 118 of the needle 112 can penetrate the piston 127. Likewise, the axial rod 126 should be comprised of a rigid material. In this embodiment, the piston 127 is disposed within the chamber 102 and between the anterior opening 110 of the chamber 102 and an end 136 of the elongate, axial rod 126 and the piston 127 is operatively coupled to the elongate axial rod 126 so that axial movement of the rod 126 results in axial movement of the piston 127. The axial rod 126 can be constructed so as to be breakable. Such a construction could be a rod having a "plus"-shaped cross section coming to a point (not shown). In this embodiment, application of force would snap the rod 126 into two pieces, thereby further rendering the syringe 100 non-reusable. Such breakable systems, as just described, are known to those of ordinary skill in the art.

In another embodiment, the means for deflecting 118 the second end 116 of the needle 112 during operation of the syringe 100 comprises a nipple 140 on the end 136 of the elongate, axial rod 126 disposed within the chamber 102. In this embodiment, the means for retracting 122 the needle 112 comprises a surface 142 of the nipple 140 facing the posterior opening 108 of the hollow chamber 102. Also, the means for engaging 120 a deflecting means 118 comprises a sloping cut 120 in the second end 116 of the needle 112 disposed within the chamber 102. And the means for engaging 124 a retracting means 122 comprises a barb 124 in a portion 144 of the second end 116 of the needle 112 disposed within the chamber. Thus, upon operation of the rod 126, the piston 127 is pierced by the second end 116 of the needle 112 to bring the nipple 140 into contact with the sloping cut 120. The sloping cut 120 radially biases the second end 116 of the needle 112 as the sloping cut 120 passes along the means for deflecting 118 the second end 116 of the needle 112.

In another preferred embodiment, the chamber 102 further comprises means for capturing 146 a retracted needle 112. In a preferred embodiment, this means for capturing 146 a retracted needle 112 comprises an intermediate section 146 of the chamber 102 proximal to the anterior opening 110. This section 146 is large enough to trap the tip of the needle 112 thereon upon full retraction of the needle 112.

In another embodiment, the present invention provides a syringe 100 wherein the intermediate section 146 comprises a circumferential wall 147 having an inner surface 148 inclined between about 10 degrees and about 90 degrees relative to the longitudinal axis A. The angle of inclination determines whether the tip of the needle 112 can slide along the inside 148 of the chamber 102 and be redirected out of the anterior opening 110 of the chamber 102. Thus, once the needle 112 is retracted it cannot be forced back out of the anterior opening 110 of the chamber 102. The syringe 100 is, therefore, non-reusable. Angles greater than 90 degrees are suitable for the purposes of the present invention. However, the possibility of an air bubble being trapped therein reduces the desirability of embodiments having angles greater than 90 degrees.

In one embodiment, an end 150 of the sloping cut 120 in the second end 116 of the needle 112 is flush with a juncture 152 of the intermediate section 146 and a passageway of the chamber 102 leading to the anterior opening 110 of the chamber 102. The positioning assures that engagement will occur at the correct moment during operation and that engagement will be sufficient to accomplish retraction.

In a preferred embodiment, the disposable hypodermic syringe 100, further comprises breakable means 154 for holding the needle 112 in place to permit retraction of the needle 112. In one embodiment, the breakable means 154 comprises an adhesive (not shown). In another embodiment, the breakable means 154 comprises a region (not shown) of the second end 116 of the needle 112 having an outer diameter greater than a diameter of the anterior opening 110 of the chamber 102. In yet another embodiment, the breakable means 154 comprises an insert mold (not shown) engaging the needle 112 with a passageway of the chamber 102 leading to the anterior opening 110 of the chamber 102. One skilled in the art would recognize that other suitable breakable means 154 are contemplated and, therefore, are included within the scope of the present disclosure.

Figures 2, 3:
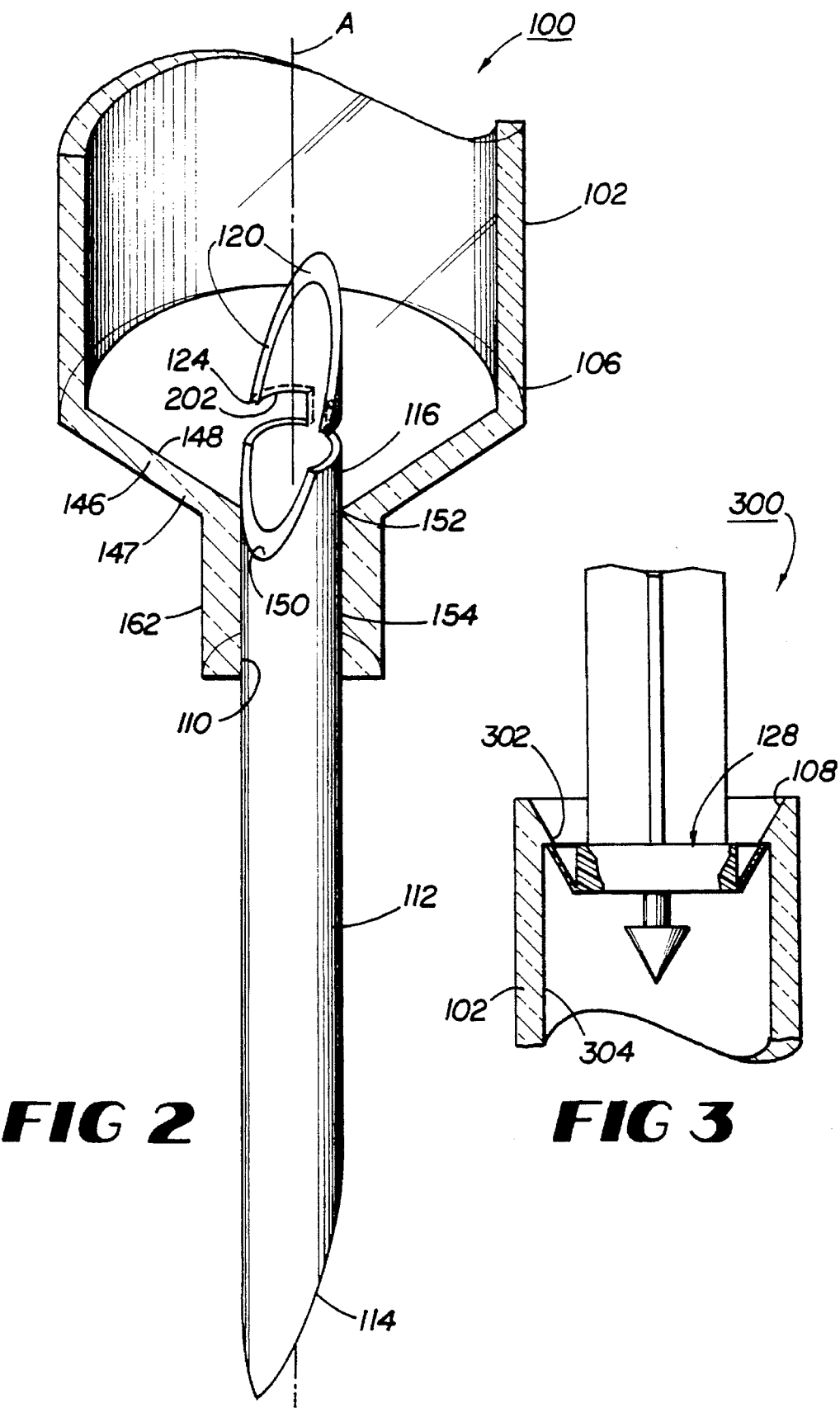
FIG. 2 shows a side plan view of the distal end of the syringe.
FIG. 3 shows a side plan view of the proximal end of the syringe showing a means for preventing complete withdrawal of the drawing and expelling means.

In another embodiment, referring now to FIG. 3, the syringe 100 further comprises, proximate to the posterior opening 108 of the chamber 102, a means 300 for preventing complete withdrawal of the drawing and expelling means 128. This means for preventing complete withdrawal 300, in a preferred embodiment, comprises a flange 302 extending into the chamber 102 from an inner surface 304 adjacent to the posterior opening 108 of the chamber 102. Likewise, a compressible flange 350 can be provided at the end of the drawing and expelling means 128. This flange 350 is inserted through the conical annulus of flange 302 and expands after insertion and thereby abuts flange 302 to prevent full extraction of the drawings and expelling means 128.

For another embodiment, referring to FIGS. 1 and 2, the barb 124 comprises a surface 202 substantially perpendicular to the longitudinal axis A of the chamber 102 for engaging, during retraction of the needle 112, the surface 142 of the nipple 140 facing the posterior opening 108 of the hollow chamber 102. Alternatively, the barb 124 comprises a surface (not shown) inclined from perpendicular relative to the longitudinal axis A of the chamber 102.

Figure 4:
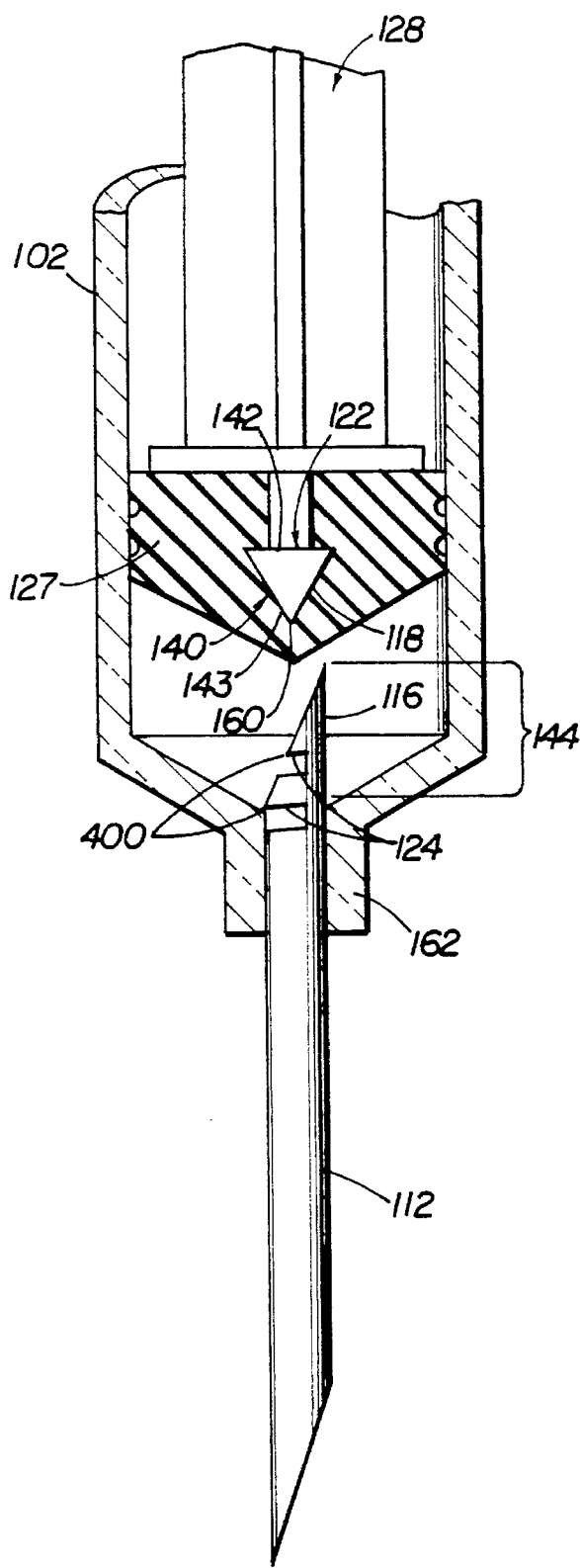

In another preferred embodiment, referring to FIGS. 1 and 4, the means for engaging 124 a retracting means 122 comprises a plurality 400 of barbs 124 in a portion 144 of the second end 116 of the needle 112. Although FIG. 4 depicts only two such barbs 124, one skilled in the art would recognize that there could be more than two barbs 124. Furthermore, the barbs 124 can be arranged in a generally saw-tooth pattern with complementary machining of the means for deflecting the needle 118 and means for retracting the needle 122. For instance, the means for deflecting 118, in one embodiment a nipple 140 could have an opposing saw-tooth pattern (not shown) upon its camming surface 143. Upon operation the saw-tooth pattern of barbs 124 would overlap with the saw-tooth pattern on the camming surface 143 and thereby provide a lock-step engagement of the second end 116 of the needle 112 to the nipple 140. Alternatively, or in addition, the means for retracting the needle 122 could serve to engage the saw-tooth pattern on the second end 116 of the needle 112. For instance, if the retracting means 122 is the surface 142 of the nipple, then this surface 142 would engage the saw-tooth pattern of barbs 124.

In a preferred embodiment, referring to FIGS. 1A through 1E, the nipple 140 is conical, having a point 160 axially directed toward the anterior opening 110 of the chamber 102.

In another embodiment, the chamber 102 further comprises a tubular extension 162 (or boss) around the anterior opening 110 to prevent the needle 112 from pivoting during retraction.

Figure 5:
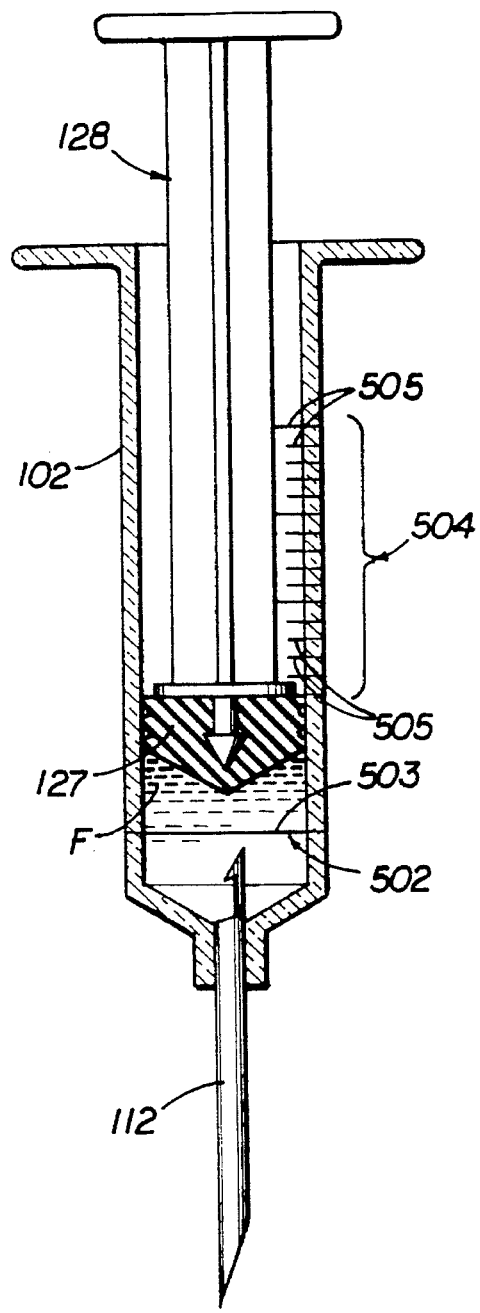
FIG. 5 shows a side plan view of the syringe with means for determining volumes of fluid depicted thereon.

In another preferred embodiment, referring now to FIG. 5, the chamber 102 is sufficiently translucent to permit the position of the piston 127 to be seen, and further comprising a first means for determining 502, from the position of the piston 127, a volume (now shown) of an injectable fluid F drawn into the chamber 102, and a second means 504 for determining, from the position of the piston 127, a volume (not shown) of the injectable fluid F expelled from the chamber 102 during an injection. In a preferred embodiment, the first means for determining 502 comprises markings 503 on the chamber 102 indicating a volume (not shown) within the chamber 102 with an offset zero position aligned with a position of the piston 127 proximal to and spaced apart from the needle 112, as shown generally in FIG. 5. In this embodiment, the second means for determining 504 comprises markings 505 on the chamber 102 indicating a volume (not shown) within the chamber 102 having a zero position aligned with a position of the piston corresponding to a forward-most position of the piston 127 (as otherwise generally shown in FIG. 1B).

Figure 1B:
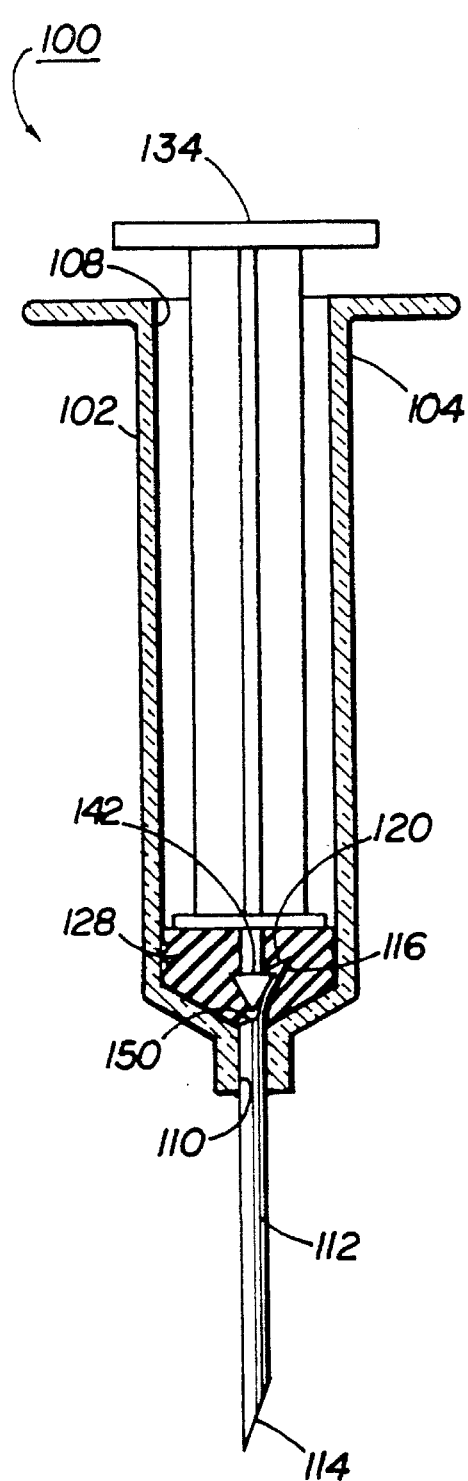
FIG. 1B shows a side plan view of the syringe of the present invention after the plunger has been fully depressed and the nipple is engaging the barb.
Figure 1C:
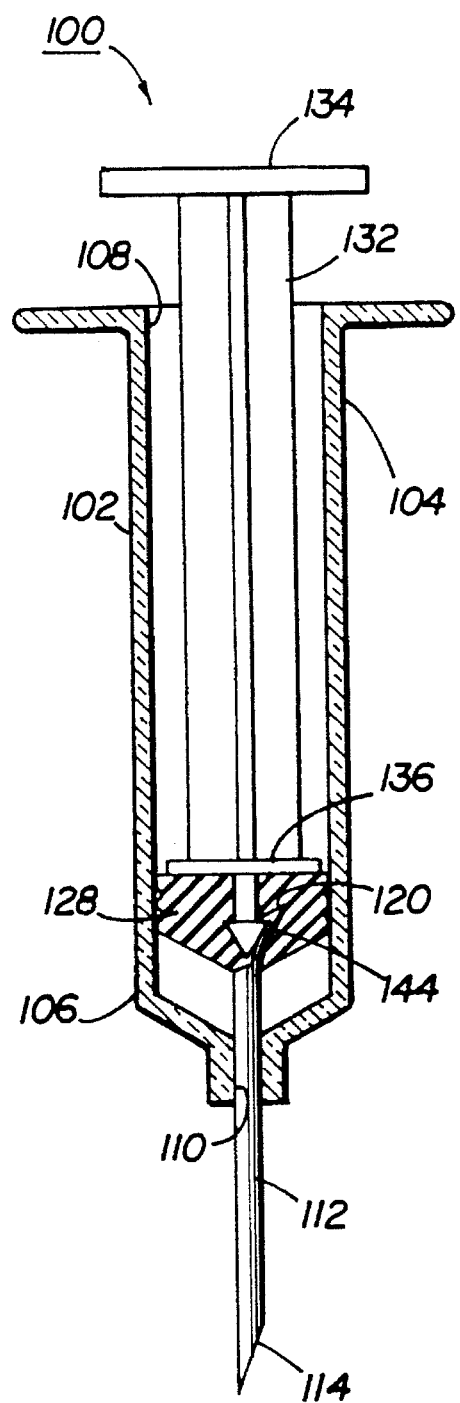
FIG. 1C shows a side plan view of the syringe of the present invention as the plunger is retracted thereby drawing the needle into the chamber.
Figures 4D, 4E:
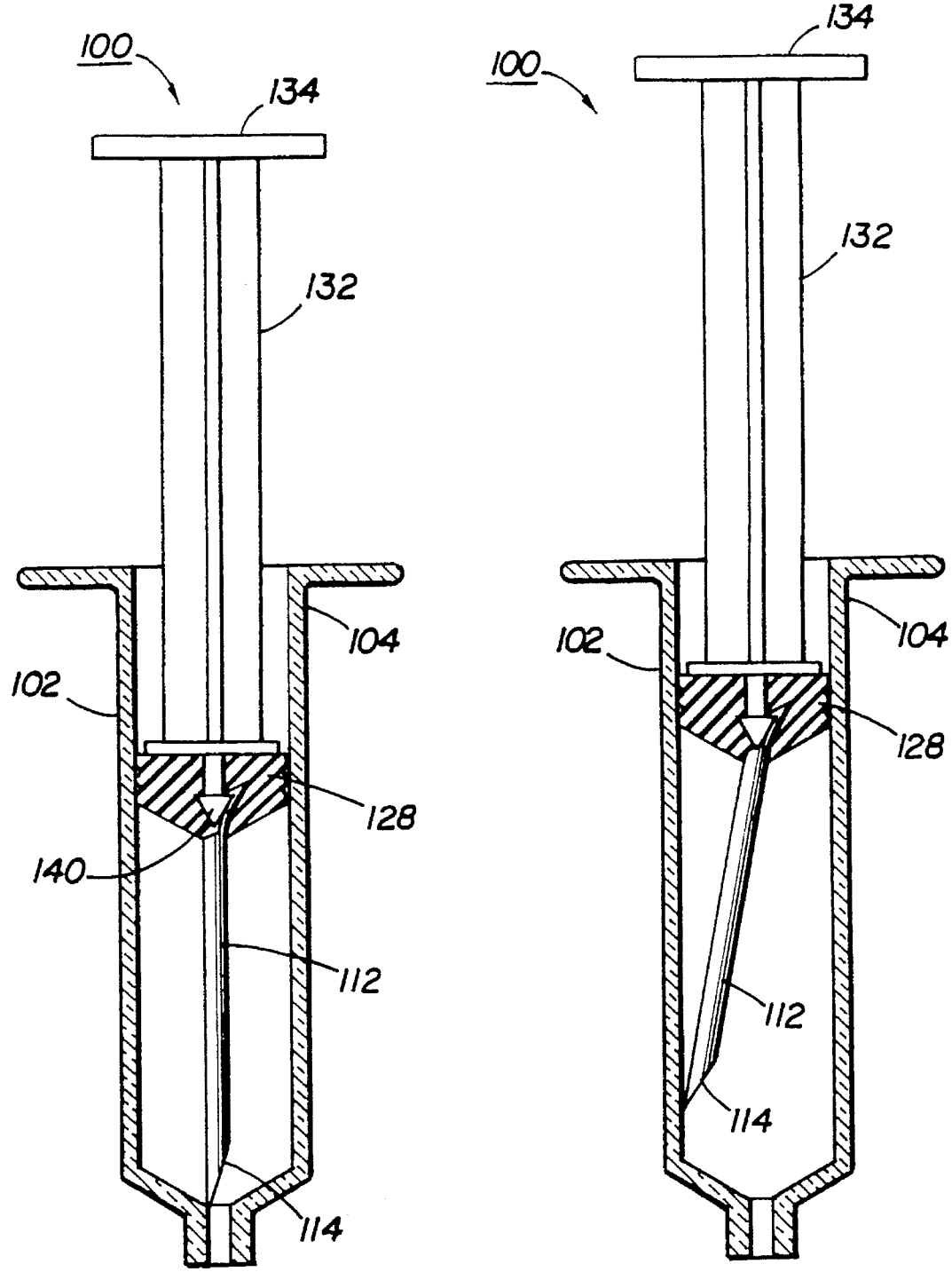
FIG. 4 shows a side plan view of the distal end of the syringe where the needle has a plurality of barbs.

The above described syringe 100 is operated as follows, referring to FIGS. 1A through 1E. Upon operation of the syringe 100 the needle 112 is retracted so that it cannot be forced back out of the syringe 100. The operation involves first piercing a flexible piston 127 at an end 130 of a plunger 128 inside the syringe 100 with an end 116 of the needle 112 inside the syringe 100. This result of this operation is depicted in FIG. 1B. After the piston 127 is pierced by the end 116 of the needle 112, the user applies a radial bias to the end 116 of the needle 112 inside the syringe 100. This biasing engages a barb 124 near the end 116 of the needle 112 inside the syringe 100 with a nipple 140 on the plunger 128. See FIG. 1B. Thus, the needle 112 is now engaged to the plunger 128. Next, the user retracts the needle 112 through an opening 110 in the syringe 100 by retracting the plunger 128. This operation is depicted in FIG. 1C. Until the first end 114 of the needle 112 passes the anterior opening 110 of the chamber 102, the axis of the needle 112 coincides with the longitudinal axis A of the chamber 102. This situation is shown in FIG. 1D, where the tip of the needle 112 is about to pass the anterior opening 110. Upon further operation and because the nipple 140 is engaged with the barb 124, the bias is relieved and causes the needle 112 to become misaligned with the opening 110 in the syringe 100, as shown in FIG. 1E.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A disposable hypodermic syringe comprising:
   (a) an elongate, rigid, hollow chamber having a longitudinal axis, a posterior opening and an anterior opening smaller than the posterior opening;
   (b) a hollow needle axially disposed within the anterior opening, having a first end outside the chamber in fluid communication with an opposed second end, the second end disposed within the chamber and in fluid communication therewith;
   (c) axially slidable means sealingly engaged within the chamber for drawing a fluid into the chamber through the first end of the needle and for expelling the fluid from the chamber through the second end of the needle, the means for drawing and expelling having a anterior end and a posterior end and comprising means for manually gripping extending out of the posterior opening of the chamber, means for deflecting the second end of the needle during operation of the syringe, and means for retracting the needle; wherein the second end of the needle includes means for engaging a deflecting means and means for engaging a retracting means, wherein the axially slidable means for drawing the fluid into the chamber and expelling the fluid from the chamber comprises an elongate, axial rod disposed within the chamber and a piercable piston for forming a slidable seal within the chamber, wherein the piston is disposed within the chamber and between the anterior opening of the chamber and an end of the elongate, axial rod and the piston is operatively coupled to the elongate axial rod so that axial movement of the rod results in axial movement of the piston, wherein
   (i) the means for deflecting the second end of the needle during operation of the syringe comprises a nipple on the end of the elongate, axial rod disposed within the chamber;
   (ii) the means for retracting the needle comprises a surface of the nipple facing the posterior opening of the hollow chamber;
   (iii) the means for engaging a deflecting means comprises a sloping cut in the second end of the needle disposed within the chamber;
   (iv) the means for engaging a retracting means comprises a barb in a portion of the second end of the needle disposed within the chamber; and
   (v) the rod is operable to cause the piston to be pierced by the second end of the needle disposed within the chamber to bring the nipple into contact with the sloping cut, thereby radially biasing the second end of the needle disposed within the chamber.

2. The disposable hypodermic syringe of claim 1, wherein the chamber further comprises means for capturing a retracted needle.

3. The disposable hypodermic syringe of claim 2, wherein the means for capturing a retracted needle comprises an intermediate section of the chamber proximate to the anterior opening.

4. The disposable hypodermic syringe of claim 3, wherein the intermediate section comprises a circumferential wall having an inner surface inclined between 10 degrees and 90 degrees relative to the longitudinal axis.

5. The disposable hypodermic syringe of claim 2, wherein an end of the sloping cut in the end of the needle is flush with a juncture of the intermediate section and a passageway of the chamber leading to the anterior opening of the chamber.

6. The disposable hypodermic syringe of claim 1, wherein the barb comprises a surface substantially perpendicular to the longitudinal axis of the chamber for engaging, during retraction of the needle, the surface of the nipple facing the posterior opening of the hollow chamber.

7. The disposable hypodermic syringe of claim 1, wherein the barb comprises a surface inclined from perpendicular relative to the longitudinal axis of the chamber.

8. The disposable hypodermic syringe of claim 1, wherein the nipple is conical, having a point axially directed toward the anterior opening of the chamber.

\* \* \* \* \*